United States Patent
Laing et al.

(10) Patent No.: US 11,110,243 B2
(45) Date of Patent: Sep. 7, 2021

(54) APPARATUS AND METHOD FOR PROVIDING GASES TO A USER

(71) Applicant: Fisher & Paykel Healthcare Limited, Auckland (NZ)

(72) Inventors: Brent Ian Laing, Auckland (NZ); David John Sims, Auckland (NZ); Mark Thomas O'Connor, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 454 days.

(21) Appl. No.: 15/896,445

(22) Filed: Feb. 14, 2018

(65) Prior Publication Data

US 2018/0169368 A1   Jun. 21, 2018

Related U.S. Application Data

(63) Continuation of application No. 14/768,555, filed as application No. PCT/NZ2014/000019 on Feb. 19, 2014, now Pat. No. 9,925,350.

(60) Provisional application No. 61/766,629, filed on Feb. 19, 2013.

(51) Int. Cl.
| | |
|---|---|
| *F16L 33/00* | (2006.01) |
| *A61M 16/08* | (2006.01) |
| *A61M 39/12* | (2006.01) |
| *F16L 37/133* | (2006.01) |
| *F16L 23/00* | (2006.01) |

(52) U.S. Cl.
CPC ........ *A61M 16/0816* (2013.01); *A61M 39/12* (2013.01); *F16L 23/006* (2013.01); *F16L 37/133* (2013.01); *A61M 2207/00* (2013.01)

(58) Field of Classification Search
CPC ......... F16L 13/10; F16L 13/13; F16L 13/146; F16L 23/024; F16L 23/0283; F16L 23/0286; F16L 23/06; F16L 23/12; F16L 47/02; F16L 47/041; F16L 37/091; F16L 37/0915
USPC .... 285/137.11, 414, 416, 915, 248–251, 340
See application file for complete search history.

(56) References Cited

U.S. PATENT DOCUMENTS

| | | | | |
|---|---|---|---|---|
| 1,354,480 | A | * | 10/1920 | Hachmann ............... F16L 31/00 285/148.13 |
| 1,370,289 | A | * | 3/1921 | Crippen ................. F16L 33/222 285/250 |
| 1,509,484 | A | * | 9/1924 | Powell .................... F16L 19/02 285/246 |
| 1,532,886 | A | * | 4/1925 | Cowles ................. F16L 33/222 285/243 |

(Continued)

OTHER PUBLICATIONS

International Search Report; PCT/NZ2014/000019; dated Jun. 3, 2014; 5 pages.
Written Opinion; PCT/NZ2014/000019; dated Jun. 3, 2014; 4 pages.

*Primary Examiner* — Aaron M Dunwoody
(74) *Attorney, Agent, or Firm* — Knobbe, Martens, Olson & Bear, LLP (57) ABSTRACT

A connector and tubing combination includes a tubing segment with an end piece, such as a tubing flange. The tubing flange can be secured within the connector by an outer sleeve and an inner sleeve of the connector. Both of the inner sleeve and the outer sleeve are located outside of the tubing flange and the tubing segment. In addition, the inner sleeve, outer sleeve and the tubing flange are mechanically connected.

23 Claims, 9 Drawing Sheets

(56) References Cited

U.S. PATENT DOCUMENTS

| | | | | |
|---|---|---|---|---|
| 2,428,189 A | * | 9/1947 | Wolfram | F16L 33/224 285/222.1 |
| 2,880,020 A | * | 3/1959 | Audette | F16L 33/222 285/255 |
| 2,933,428 A | * | 4/1960 | Mueller | B29C 65/561 156/73.5 |
| 3,078,109 A | * | 2/1963 | Reed | F16L 33/24 285/251 |
| 3,097,866 A | * | 7/1963 | Iversen | F16L 33/222 285/18 |
| 3,236,543 A | * | 2/1966 | Mueller | F16L 33/006 285/2 |
| 3,776,996 A | * | 12/1973 | Cameron et al. | B29C 45/14754 264/242 |
| 4,103,943 A | * | 8/1978 | Curtin | F16L 47/02 285/419 |
| 4,591,194 A | * | 5/1986 | Tash | F16L 33/2076 285/249 |
| 4,621,937 A | * | 11/1986 | Maccuaig | B60T 11/04 285/192 |
| 4,753,458 A | * | 6/1988 | Case | F16L 37/0987 285/319 |
| 4,802,696 A | * | 2/1989 | Chohan | F16L 37/091 285/317 |
| 4,810,010 A | * | 3/1989 | Jones | F16C 3/026 285/222.4 |
| 4,842,309 A | * | 6/1989 | LaVene | F16L 37/0842 285/319 |
| 4,929,002 A | * | 5/1990 | Sauer | F16L 33/213 285/148.13 |
| 4,938,511 A | * | 7/1990 | Kersting | F16L 37/16 285/312 |
| 5,042,849 A | * | 8/1991 | Kersting | F16L 33/24 285/312 |
| 5,087,081 A | * | 2/1992 | Yoon | A47L 15/4217 285/148.19 |
| 5,096,235 A | * | 3/1992 | Oetiker | F16L 37/0987 285/308 |
| 5,131,687 A | * | 7/1992 | Marchou | F16L 33/22 285/23 |
| 5,141,263 A | * | 8/1992 | Varden | F16L 37/0985 285/243 |
| 5,195,787 A | * | 3/1993 | Bartholomew | F16L 37/0987 285/317 |
| 5,335,943 A | * | 8/1994 | Duryea | F16L 33/00 285/12 |
| 5,344,195 A | * | 9/1994 | Parimore, Jr. | F16L 19/0231 285/340 |
| 5,375,887 A | * | 12/1994 | Johnson | E03C 1/021 285/12 |
| 5,380,051 A | * | 1/1995 | Breuhan | F16L 37/096 285/307 |
| 5,449,207 A | * | 9/1995 | Hockett | F16L 37/101 285/286.2 |
| 5,489,125 A | * | 2/1996 | Hohmann | F16L 37/138 285/308 |
| 5,536,049 A | * | 7/1996 | Coules | F16L 33/227 285/137.11 |
| 5,709,413 A | * | 1/1998 | Salyers | F16L 33/223 285/219 |
| 5,901,987 A | * | 5/1999 | Godeau | F16L 21/03 285/148.19 |
| 6,412,826 B1 | * | 7/2002 | Kulevsky | F16L 37/098 285/305 |
| 6,543,814 B2 | * | 4/2003 | Bartholomew | F16L 37/0987 285/319 |
| 6,688,654 B2 | * | 2/2004 | Romero | F16L 37/0987 285/308 |
| 7,067,032 B1 | * | 6/2006 | Bremont | F16L 13/103 156/272.2 |
| 9,022,431 B2 | * | 5/2015 | Furst | F16L 19/0653 285/251 |
| 9,925,350 B2 | | 3/2018 | Laing et al. | |
| 2003/0193190 A1 | | 10/2003 | Werth | |
| 2004/0012198 A1 | * | 1/2004 | Brotzell | E21B 17/02 285/249 |
| 2004/0137778 A1 | * | 7/2004 | Mattheeuws | F16L 33/227 439/352 |
| 2004/0183302 A1 | | 9/2004 | Allen et al. | |
| 2005/0035597 A1 | | 2/2005 | Bamberger et al. | |
| 2005/0146139 A1 | * | 7/2005 | Huybrechts | F16L 23/0286 285/368 |
| 2007/0213690 A1 | * | 9/2007 | Phillips | A61M 1/3659 604/533 |
| 2008/0061551 A1 | * | 3/2008 | Simmons | F16L 19/025 285/249 |
| 2009/0302596 A1 | * | 12/2009 | Keller | A61M 39/12 285/21.3 |
| 2010/0194102 A1 | | 8/2010 | Keeling | F16L 37/091 285/305 |
| 2011/0140409 A1 | * | 6/2011 | Sisk | F16L 47/041 285/24 |
| 2011/0209788 A1 | * | 9/2011 | Kim | F16L 13/0209 137/801 |
| 2012/0098253 A1 | * | 4/2012 | Folcarelli | B29C 45/14614 285/240 |
| 2015/0198278 A1 | * | 7/2015 | Clements | F16L 19/025 285/93 |
| 2016/0001031 A1 | | 1/2016 | Laing et al. | |
| 2016/0003394 A1 | * | 1/2016 | Reasoner | F16L 37/0982 251/149.6 |
| 2017/0114935 A1 | * | 4/2017 | Kujawski, Jr. | B25B 27/0028 |

* cited by examiner

APPARATUS AND METHOD FOR PROVIDING GASES TO A USER

FIELD OF THE INVENTION

The present application generally relates to connectors that attach to resilient tubing. More particularly, certain features, aspects and advantages of the present application relate to connectors used to provide an end connection to tubing components.

BACKGROUND OF THE INVENTION

Tubing connectors are used to join flexible tubing to various components in the breathing treatment fields. Because the tubing is generally a softer, flexible material and the connector is generally a harder plastic material, these connectors generally are joined to the tubing using adhesives or the like. In situations where the connectors are joined to the tubing without the use of adhesives, it has been found that material creep can loosen the union between the connectors and the tubing over time.

SUMMARY OF THE INVENTION

Accordingly, this is a need for a connector to can securely join to an end of tubing.

The connector can be formed such that it is located entirely outside of the tubing such that the end of the tubing is not obstructed by the connector. Such a configuration advantageously allows use of the tubing with standard barbed air connections even with the connector installed on the end of the tubing.

The connector can be mechanically secured (e.g., snap fit) together. By using a mechanical coupling, the use of adhesives, overmolding or the like can be avoided, if desired. By avoiding adhesives and the like, compatibility of the adhesive materials or the like does not present any issues. Furthermore, without the use of adhesives, solvents or overmolding, the assembly time can be shortened, which improves throughput for manufacturing In some configurations, a tubing and connector combination can comprise a tubing segment and a tubing flange that are connected together, an inner sleeve, and an outer sleeve with the inner sleeve and the outer sleeve being mechanically secured together and being positioned outside of a flow path through the tubing segment and the tubing flange.

In some configurations, the outer sleeve comprises an inner passage that tapers in the proximal direction and the inner sleeve comprises a proximal portion with distally-extending slots that allow compression of the proximal portion of the inner sleeve.

In some configurations, the tubing flange comprises an outer peripheral surface and an inner surface of the inner sleeve forms a seal around the outer peripheral surface of the tubing flange.

In some configurations, the inner sleeve comprises a distal portion having a structure configured to mate with a complementary structure. In some configurations, the distal portion is formed along an internal surface. In some configurations, the inner sleeve comprises an inner shoulder, the inner shoulder and a portion of the tubing segment and tubing flange abutting following connection and the structure configured to mate with the complementary structure is positioned entirely distal of the shoulder. In some configurations, at least a portion of the structure configured to mate with the complementary structure is positioned directly adjacent to the shoulder.

In some configurations, the outer sleeve comprises a plurality of prongs, the prongs extending in a distal direction and defining a tapering opening with a larger proximal crossing dimension and a smaller crossing dimension distally of the larger proximal crossing dimension. In some such configurations, a portion of the prongs intersected by the smaller crossing dimension and an inner surface of the outer sleeve are separated by a gap.

In some configurations, the outer sleeve comprises a plurality of prongs, at least a portion of one or more of the prongs being adapted to elastically deflect radially outward.

In some configurations, the outer sleeve comprises a plurality of prongs that are configured to deform to allow insertion of the tubing segment and tubing flange in a first direction but abut against a portion of the tubing segment and tubing flange to reduce the likelihood of withdrawal of the tubing segment and tubing flange in a second direction.

In some configurations, the outer sleeve comprises a plurality of prongs that are symmetrically positioned about an inner surface of the outer sleeve.

BRIEF DESCRIPTION OF THE DRAWINGS

These and other features, aspects and advantages of the present invention now will be described with reference to the following figures, which are not intended to be limiting.

DETAILED DESCRIPTION OF THE INVENTION

Figure 1:
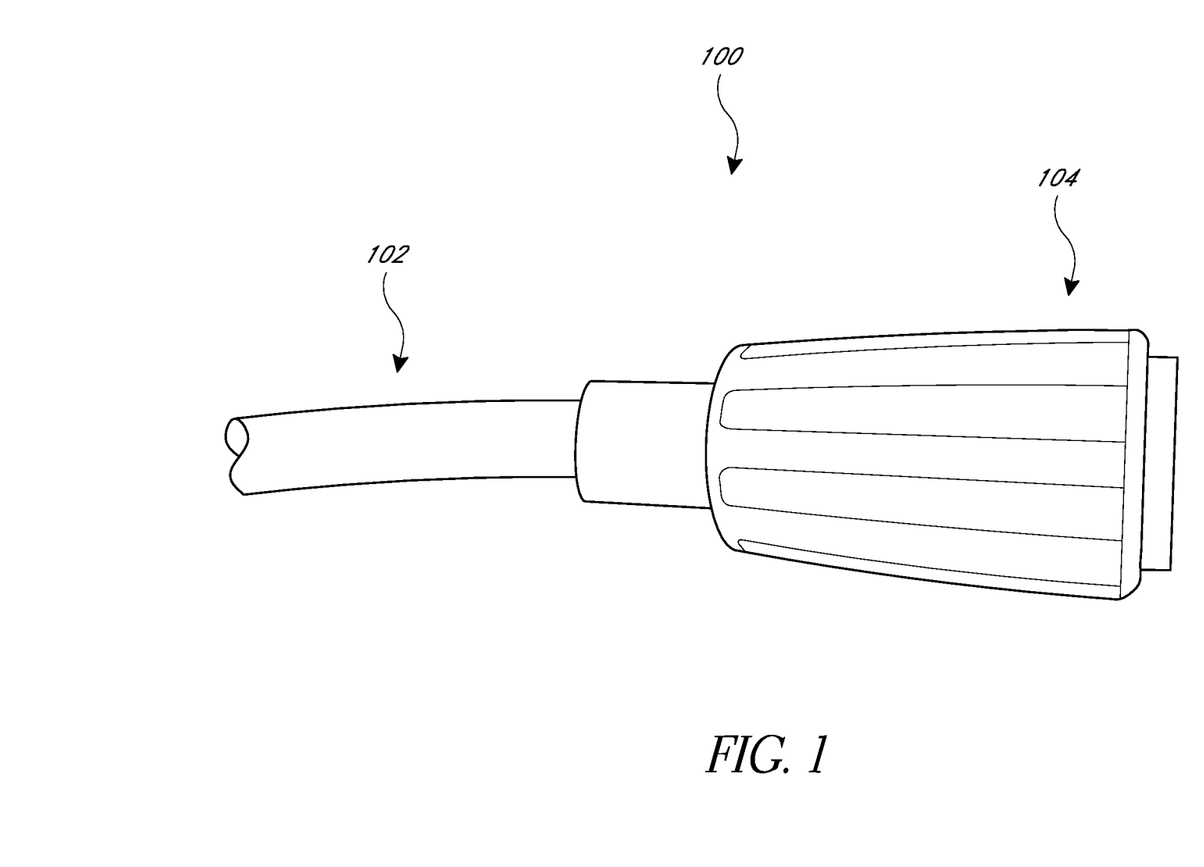
FIG. 1 is a side elevation view of a connector and tubing combination that is arranged and configured in accordance with certain features, aspects and advantages of the present invention.

With reference initially to FIG. 1, a connector and tubing combination 100 is illustrated therein. The combination 100 generally comprises a segment of tubing 102 and a connector assembly 104. When assembled, the combination 100 can be used to couple the tubing to a connector of another component. In some configurations, the combination can couple to a proprietary connector while also enabling connection to a standard barbed connection, for example but without limitation.

Figure 2:
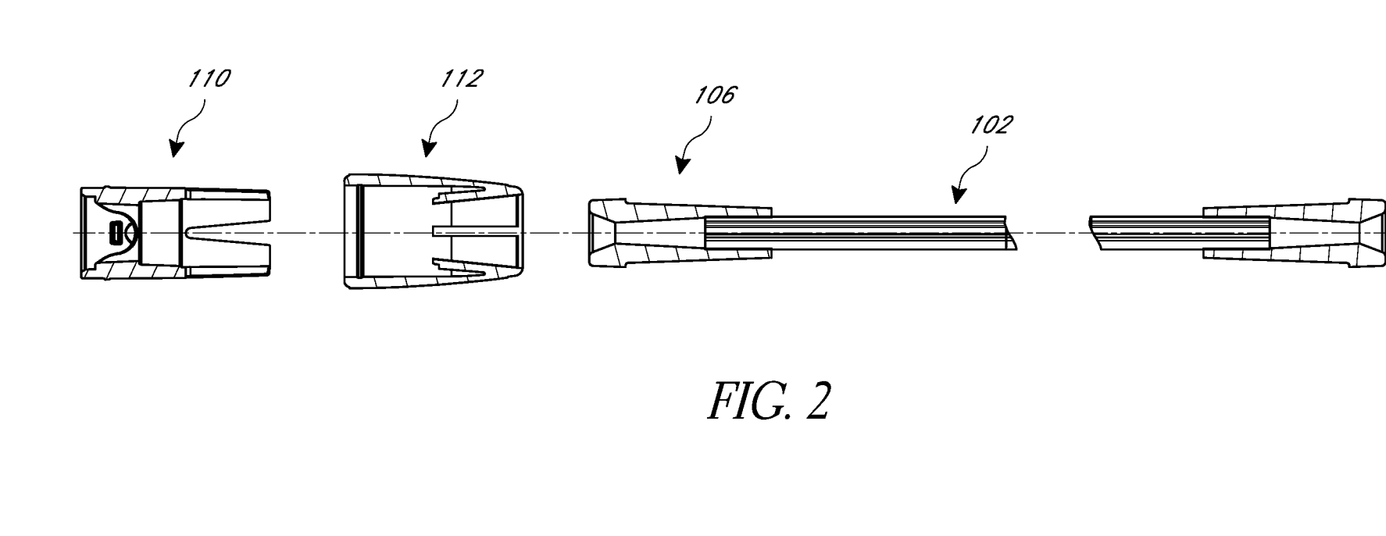
FIG. 2 is an exploded view of the combination of FIG. 1, illustrating a segment of tube, an end adapter, an inner sleeve and an outer sleeve.

With reference to FIG. 2, in some configurations, the tubing 102 can include a tubing flange 106 or other end component. The tubing 102 and the tubing flange 106 can be formed from any suitable material. In the illustrated configuration, the two are formed from polyvinyl chloride materials and can be solvent bonded together. While other configurations are possible, forming the tubing 102 and the tubing flange 106 from alike materials facilitates solvent bonding, which results in a very strong and lasting connection between the two components 102, 106. In other configurations, the tubing 102 can include an end that is sized and configured for use with the connector assembly 104. For example, the tubing could include a shoulder, ridge, protrusion or the like. In some configurations, the tubing and the tubing flange can be an integral component, such as when formed as a single piece.

With reference still to FIG. 2, the illustrated connector assembly 104 comprises an inner sleeve 110 and an outer sleeve 112. When the inner sleeve 110 is positioned over the tubing flange 106 and the outer sleeve 112 is joined to the inner sleeve 110, the connector assembly 104 can be locked onto the tubing 102. In some configurations, when the inner sleeve 110 and the outer sleeve 112 are locked together, the two components 110, 112 form a mechanically mating retention system that locks onto the tubing 102. In some configurations, the mechanically mating retention system can be fit together without the use of tools, without the use of adhesives, bonding agents or overmolding, for example but without limitation. Such a system can simplify manufacture, can reduce time to manufacture (e.g., eliminate a curing period) while also reducing or eliminating material compatibility issues and the like. Furthermore, as will be described, the mating retention system can adjust such that a grip on the tubing is not substantially weakened due to material creep over time.

Figure 3:
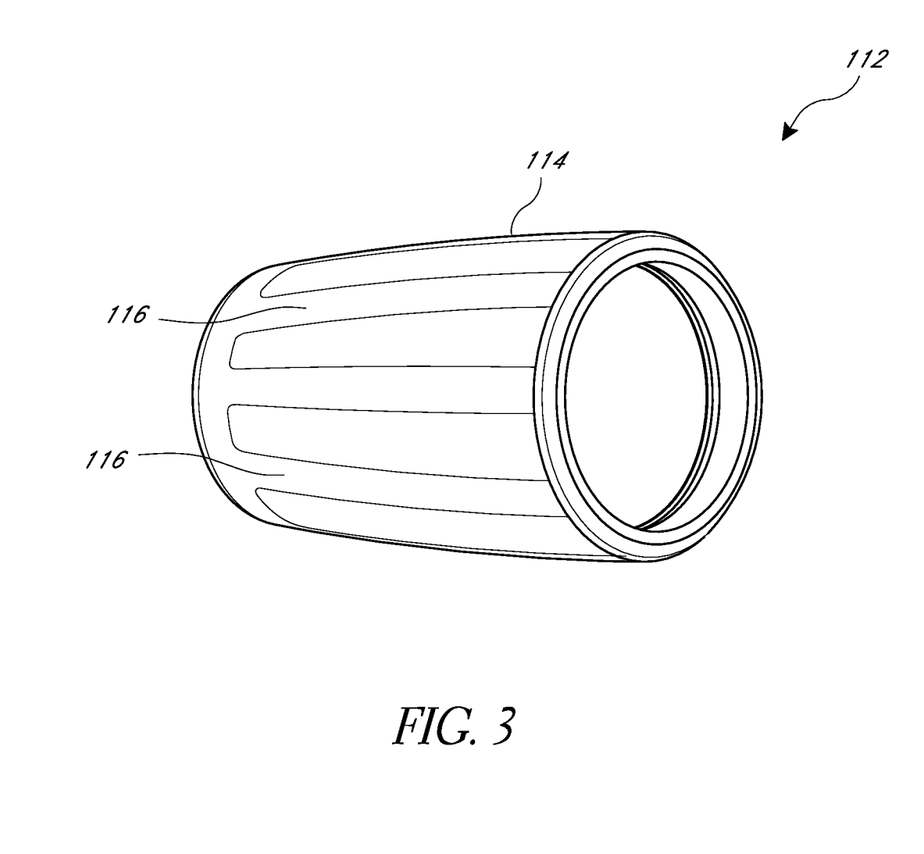
FIG. 3 is a side view of the outer sleeve of FIG. 2.
Figure 4:
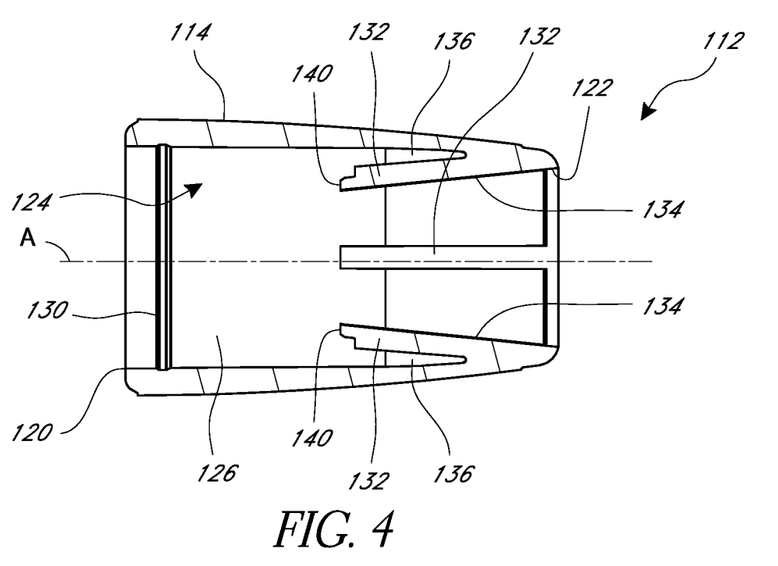
FIG. 4 is a sectioned side view of the outer sleeve of FIG. 2.

With reference now to FIGS. 3 and 4, the outer sleeve 112 will be described. As illustrated, the outer sleeve 112 comprises an outer surface 114. The outer surface 114 can have any suitable shape. The shape of the illustrated outer surface 114 provides an aesthetic appearance and has been configured to present a desired industrial design. In some configurations, the outer surface 114 can be generally cylindrical. In the illustrated configuration, the outer surface 114 has a generally cylindrical distal portion and tapers in a proximal direction. The outer surface 114 can have any suitable surface texture or structures. In the illustrated configuration, the outer surface 114 comprises generally axially extending ribs 116.

With reference to FIG. 4, the outer sleeve 112 comprises a distal opening 120 and a proximal opening 122. A passage 124 can extend from the distal opening 120 to the proximal opening 122. In the illustrated configuration, an inner surface 126 can define at least a portion of the lumen or passage 124. The passage 124 can taper such that a distal end of the passage 124 has a larger inner diameter than a proximal end of the passage 124. In some configurations, a proximal portion of the passage 124 has a greater reduction in diameter than distally of that proximal portion.

A groove 130 can be positioned along the inner surface 126. In the illustrated configuration, the groove 130 can be positioned close to the distal opening 120. The groove 130 generally comprises a recess in the inner surface 126. While the illustrated groove 130 is generally cylindrical, circular, uninterrupted or the like, in some configurations, the groove 130 can be formed of multiple discrete segments or the like.

With continued reference to FIG. 4, the illustrated outer sleeve 112 comprises one or more prongs 132. In the illustrated configuration, the outer sleeve 112 comprises four prongs 132. Other numbers of prongs 132 can be used. In some configurations, the prongs 132 are positioned symmetrically about the passage 124.

The prongs 132 extend distally in the illustrated configuration. In some configurations, the prongs 132 extend distally from near the proximal opening 122. The prongs can be configured such that at least a portion can elastically deform in a radially outward direction. In some configurations, the most distal portions of the prongs 132 can elastically deflect radially outward.

Each of the prongs 132 has an inner surface 134. The inner surface 134 can slope toward an axial center A of the passage 124. The sloping surfaces 134 define a narrowing portion within the passage 124. A gap 136 can be positioned between at least a distal portion of each prong 132 and the inner surface 126. The gap 136 allows at least a distal portion of the associated prong 132 to deflect outwardly away from the axial center A. In some configurations, the inner surfaces 134 of the prongs 132 define a crossing dimension (e.g., diameter), with a larger crossing dimension being positioned proximally and a smaller crossing dimension being positioned distally of the larger crossing dimension. The gaps 136 preferably is positioned at least in the region that is intersected by a plane defined along the smallest crossing dimension.

As shown in FIG. 4, each prong 132 has a distal end 140. In some configurations, the distal end 140 can taper smoothly toward the distal end 140. In some configurations, including the illustrated configuration, the distal end 140 can have a step-like appearance such that the distal end 140 has a recess formed along the outer surface that defines, in part, the gap 136. In some configurations, the distal end 140 does not taper at all.

Figure 5:
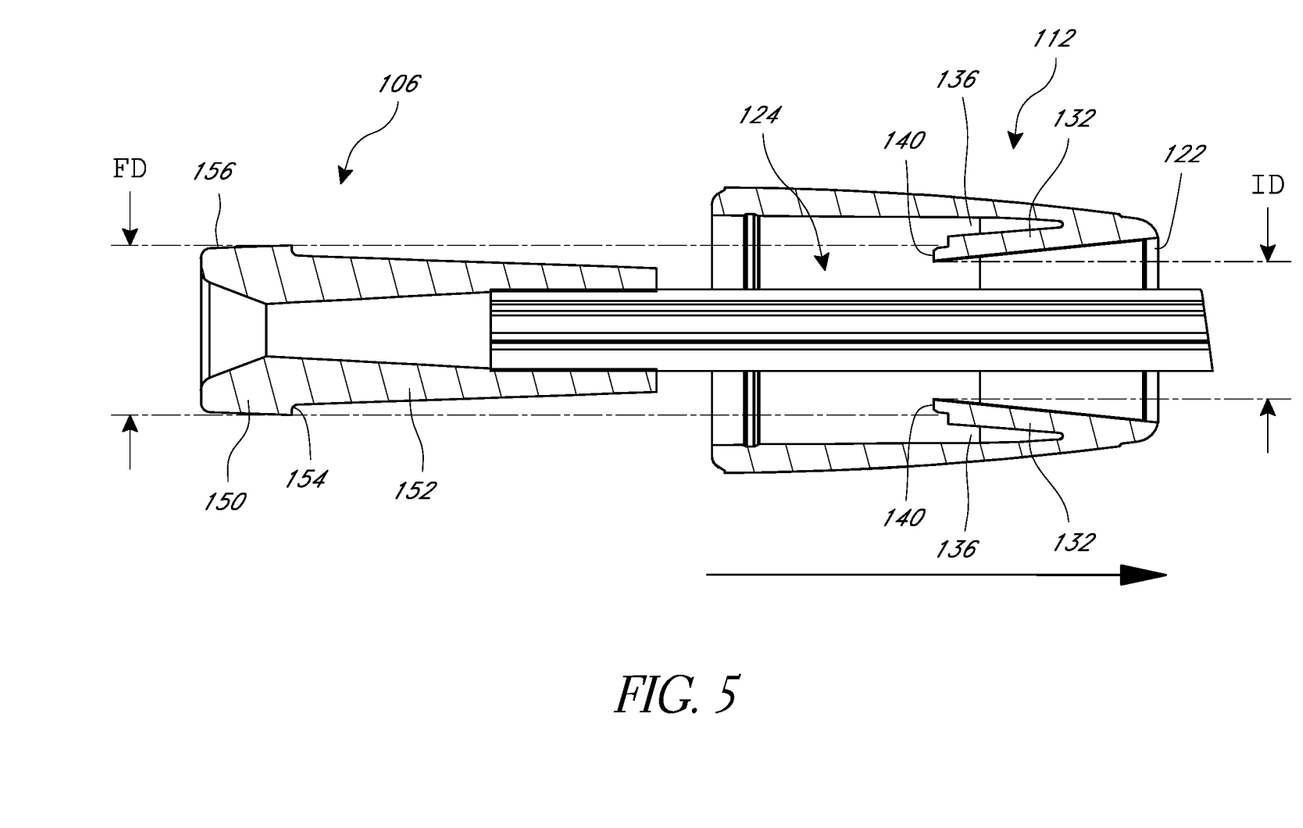
FIG. 5 is a sectioned side view of the end adapter and the outer sleeve of FIG. 2.

With reference now to FIG. 5, the tubing flange 106 can be inserted through the outer sleeve 112 along the passage 124. The tubing flange 106 can have a head portion 150 and a tapering neck portion 152. The neck portion 152 can taper in a proximal direction such that the outer diameter of the neck portion 152 is greater in a distal region compared to the outer diameter of the neck portion in the proximal portion. A transition, shown as a shoulder 154, can be present between the head portion 150 and the tapering neck portion 152.

The proximal opening 122 is larger than an outer diameter FD of the head 150 of the tubing flange 106. Thus, the head 150 can pass through the proximal opening 122. An inner diameter ID defined by the spacing between the distal ends 140 of the prongs 132 when relaxed can be less than the outer diameter FD of the head 150. Thus, in the illustrated configuration, the distal ends 140 of the prongs 132 can deflect outward, which reduces the gap 136 while the head 150 passes through the prongs 132. Once the head 150 clears the distal end of the prongs 132, the prongs 132 can return toward the relaxed position shown in FIG. 5. During assembly, the outer sleeve 112 can be slid over the tubing flange 106 and left on the segment of tubing 102.

Figure 6:
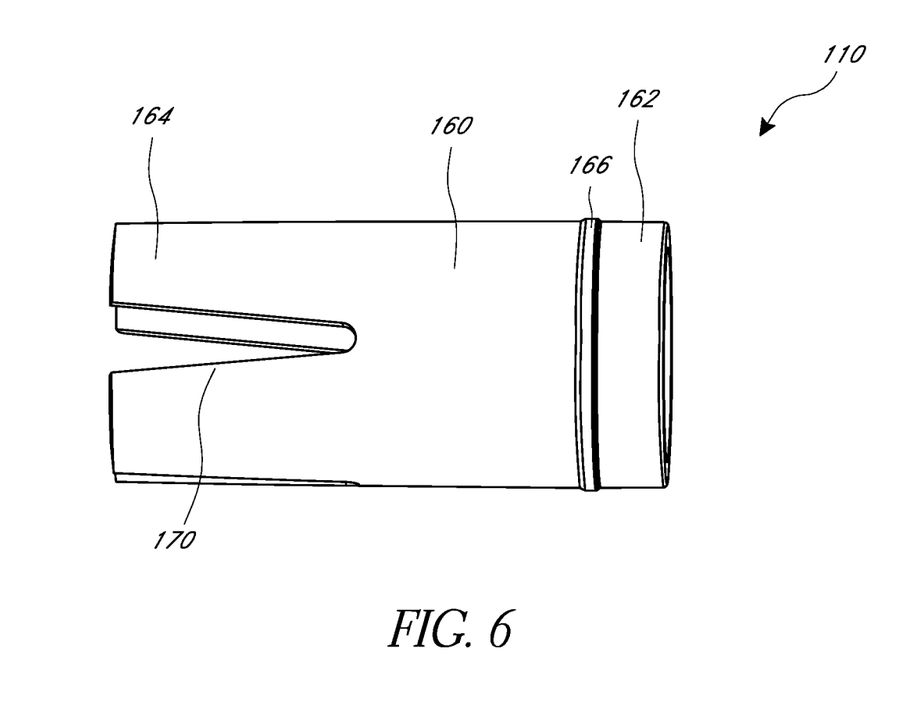
FIG. 6 is a side view of the inner sleeve of FIG. 2.
Figure 7:
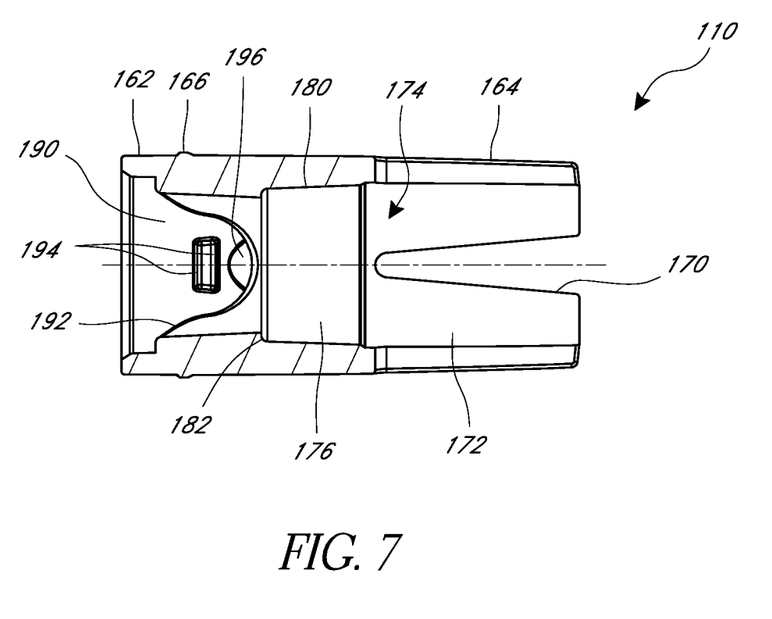
FIG. 7 is a sectioned side view of the inner sleeve of FIG. 2.

With reference now to FIGS. 6 and 7, the inner sleeve 110 will be described in greater detail. The inner sleeve 110 comprises an outer surface 160. The outer surface can be generally cylindrical. In the illustrated configuration, the outer surface 160 comprises a distal portion 162 and a proximal portion 164. The proximal portion tapers slightly such that an outer diameter of the proximal portion 164 reduces in a distal direction. In some configurations, the taper reflects a draft angle used in formation of the inner sleeve 110. Other configurations are possible.

In the illustrated configuration, the outer surface 160 comprises a protrusion 166. The protrusion 166 can be positioned along the distal portion 162. The protrusion 166 is designed to cooperate with the groove 130 along the inner surface 126 of the outer sleeve 112. Other configurations are possible. Some of those configurations can include interlocking components. Accordingly, in some configurations, the protrusion 166 can be positioned along the inner surface of the outer sleeve 112 while the groove 130 can be positioned along the outer surface 160 of the inner sleeve 110. Such a configuration, however, is less manufacturable. Nevertheless, the groove 130 and the protrusion 166 can be configured in any suitable manner. The groove 130 and the protrusion 166 can be used to secure the inner and outer sleeves 110, 112 in relative axial position.

With reference now to FIG. 7, the proximal portion 164 can include one or more slots 170. The slots 170 can extend inwardly from an extreme proximal end of the inner sleeve 110. The slots 170 can be configured to accommodate the prongs 132. In some configurations, the number of slots 170 corresponds to the number of prongs 132. In some configurations, the slots 170 taper in a distal direction from the extreme proximal end. In the illustrated configuration, the slots 170 taper and assume a V-shaped configuration. Preferably, the V-shaped configuration of each of the slots 170 has a cross dimension that is slightly larger than a corresponding dimension of the associated prong 132. Thus, as the inner sleeve 110 is inserted further into the tapering passage 124 of the outer sleeve 112, the proximal portion 164 can compress along the slots 170 with the prongs 134 of the outer sleeve 112 positioned within the slots 170.

Figure 8:
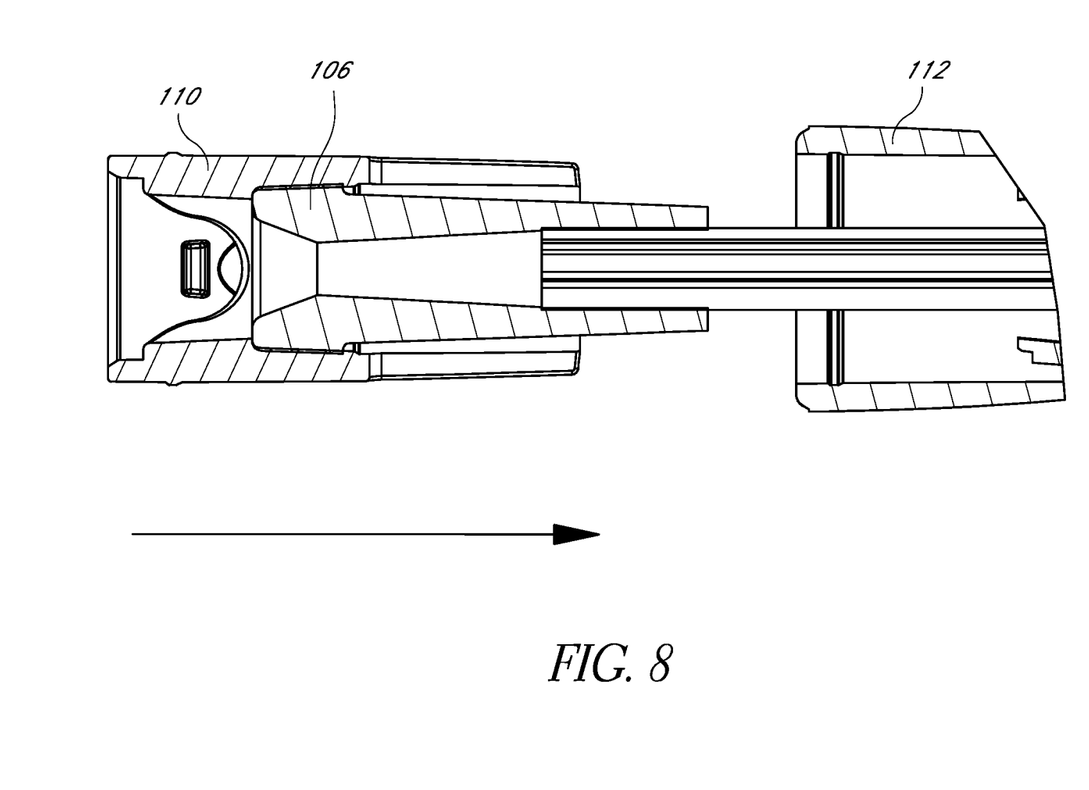
FIG. 8 is a sectioned side view of the inner sleeve, the outer sleeve and the end adapter of FIG. 2.

The inner sleeve 110 has an inner surface 172 that defines a passage 174. The passage includes a receptacle 176. The receptacle 176 can be sized and configured to receive the head portion 150 of the tubing flange. In some configurations, the receptacle 176 can comprise an inner wall 180 that is sized and configured to provide an interference fit with an outer surface 156 of the head portion 150. The receptacle can include a shoulder 182 at a distal end such that the distal movement of the head portion 150 relative to the inner sleeve 112 can be limited, as shown in FIG. 8. In some configurations, the shoulder 182 can provide compression to the distal face of the tubing flange 106 and can oppose forces from the prongs 132.

At a distal end of the inner sleeve 110, the inner sleeve 110 can be provided with any suitable connector configuration. In some configurations, the distal portion 162 of the inner sleeve 110 may be blank without any internal or external features. In some configurations, the distal portion 162 of the inner sleeve 110 can be configured to interlock with a complementary connector. In some configurations, the distal portion 162 of the inner sleeve 110 can be configured to interlock with a connector portion such as that shown and described in U.S. Design Pat. application No. 29/429,467, filed on Aug. 10, 2012 and entitled Connector Assembly, U.S. Design Pat. application No. 29/433,930, filed on Oct. 6, 2012 and entitled Connector Assembly as well as International Application No. PCT/NZ2012/000142, filed on Aug. 10, 2012 and entitled Conduit Connector for a Patient Breathing Device, each of which is hereby incorporated by reference.

With reference still to FIG. 7, the inner surface of the distal portion 162 may comprise a contoured recessed region 190. The contoured recessed region 190 comprises a proximal-most portion that is directly adjacent to the shoulder 182. The contoured recessed region 190 comprises a U-shaped appearance that opens in an upwardly direction. The recessed region 190 can be formed by a protrusion 192 from the inner wall of the distal portion 162. A pair of generally parallel tabs 194 can be positioned within the contoured recessed region 190. In the illustrated configuration, the tabs 194 can be positioned closer to the proximal end of the recessed region than the distal end. Furthermore, in the illustrated configuration, a further recess 196 can be positioned between the tabs 194 and the proximal end of the recessed region 190.

Figure 9:
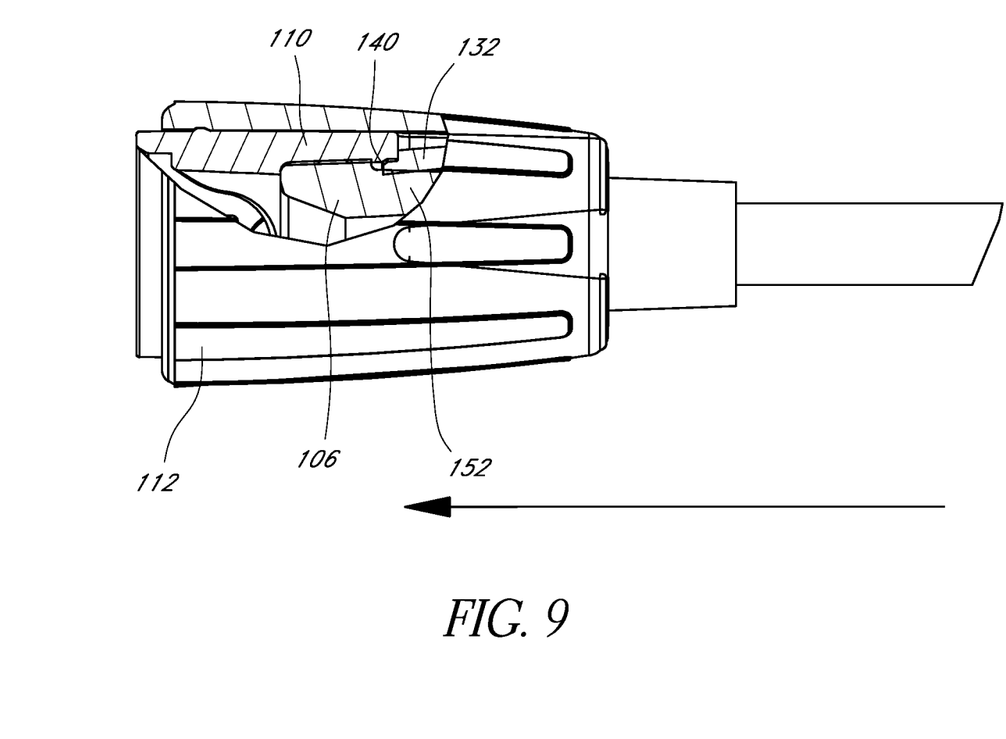
FIG. 9 is a partially sectioned side view of the assembled inner sleeve, outer sleeve and the end adapter of FIG. 2.

With reference now to FIGS. 5, 8 and 9, an assembly process for the tubing and connector combination 100 will be described. The assembly process can take place all at a single end of the tubing segment 102. As shown in FIG. 5, the tubing segment 102 can be provided with the tubing flange 106 already connected. The tubing flange 106 can be connected to the tubing segment 102 in any suitable manner. In some configurations, the tubing flange 106 can be inserted into the tubing segment 102 and solvent bonded into position within the tubing segment 102.

In the illustrated configuration, the assembled tubing flange 106 and tubing segment 102 is inserted through the passage 124 of the outer sleeve 124. The tubing flange 106 is inserted through the proximal opening 122 of the outer sleeve 124. Because the outer diameter of the illustrated tubing flange 106 is larger than an inner diameter defined by the prongs 132, the prongs 132 are deflected outward. As the prongs 132 deflect outward, the gaps 136 become smaller but sufficient movement of the prongs 132 is allowed by the gaps 136 to let the tubing flange 106 pass through the opening defined between the prongs 132. The outer sleeve 112 can be slid onto the tubing segment 102 and released.

As shown in FIG. 8, the tubing flange 106 can be slid distally into the passage 174 of the inner sleeve 110. Further distal movement of the tubing flange 106 into the inner sleeve 110 can place the head portion 150 within the receptacle 176. In this position, the distal end of the head portion 150 seats against the shoulder 182 defined within the inner sleeve 110. In some configurations, the head portion 150 can be secured in position within the receptacle 176 with an interference fit. In some configurations, a fluid-tight seal or a substantially fluid-tight seal can be defined by the interface of the tubing flange 106 and the inner sleeve 110. In some configurations, the outer surface 156 of the head portion 150 can form a fluid-tight seal or a substantially fluid-tight seal with the adjoining portion of the receptacle.

With tubing flange 106 inserted into the inner sleeve 110, the combined flange 106 and inner sleeve 110 can be slid back into the outer sleeve 112 as shown in FIG. 8. In some configurations, a loose fitting might be accomplished with the assembly being finger tightened into position. With the components secured together in a finger tight relationship, the tubing and connector combination 100 can be placed into a fixture that completes the snap fit assembly so that the components assume the relationship shown in FIG. 9.

With reference now to FIG. 9, the outer sleeve 112 substantially surrounds and encases the inner sleeve 110. The inner sleeve 110 overlies at least the head portion 150 of the tubing flange 106. The prongs 132 can be positioned within the slots 170 and, where the passage 124 of the outer sleeve 112 tapers, the edges of the slots 170 can close alongside of the prongs 132 as the proximal portion 164 reduces in diameter.

In the illustrated configuration, at least a portion of one or more of the prongs 132 squeezes against the neck portion 152 of the tubing flange 106. In some configuration, one or more of the distal ends 140 can be sandwiched between the inner sleeve 110 and the tubing flange 106. In this manner, the prongs 132 and the inner sleeve 110 can squeeze against the tubing flange 106. In some configurations, the prongs 132 and the inner sleeve 110 can compress the material of the tubing flange 106. In some configurations, deflection of the prongs 132 can provide a retention force that accommodates creep within the materials over time. In some configurations, the prongs 132, instead of squeezing the tubing in a radial direction or in addition to squeezing the tubing in a radial direction, may interact with the shoulder 154 at the proximal end of the head portion 150 such that the prongs 132 limit the axial movement of the head portion 150 in a proximal direction while the shoulder 182 of the inner sleeve limits the axial movement of the head portion 150 is a distal direction. Thus, in some configurations, a protrusion (e.g., the head portion 150) of the tubing can be captured in an axial direction between a portion of the inner sleeve 110 (e.g., the shoulder 182) and a portion of the outer sleeve 112 (e.g., the prongs 132).

With the inner sleeve 110 fully pressed into the outer sleeve 112, the protrusion 166 of the inner sleeve is received within the groove 130 of the outer sleeve 112. The protrusion 166 and the groove 130 provide a snap-fit connection between the inner sleeve 110 and the outer sleeve 112. While a snap-fit is used in the illustrated configuration, other manners of joining the inner sleeve 110 and the outer sleeve 112 can be used. For example, ratcheting hooks, compression fits or the like can be used.

In the illustrated configuration, a portion of the inner sleeve 110 can protrude outward from the outer sleeve 112. As shown, even when fully connected, the illustrated inner sleeve 110 extends slightly outward from the distal end. Other configurations are possible.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

The invention claimed is:

1. A connector assembly comprising:
a tubing flange comprising a proximal end and a distal end, the tubing flange configured to connect to an end of a tube at the proximal end of the tubing flange, the tubing flange comprises a head portion at the distal end of the tubing flange and a tapering neck portion extending from the head portion to the proximal end, the tubing flange defining a gas passageway through the head portion and the tapering neck portion;
an inner sleeve comprising a distal portion and a proximal portion, the proximal portion of the inner sleeve comprises a plurality of slots, wherein each of the plurality of slots extends distally from a proximal end of the inner sleeve, the inner sleeve comprising a receptacle sized and configured to receive the head portion of the tubing flange, the receptacle comprising a shoulder configured to abut the distal end of the tubing flange, wherein when assembled, an inner wall of the receptacle provides an interference fit with an outer surface of the head portion;
an outer sleeve mechanically secured to the inner sleeve such that the outer sleeve and inner sleeve are locked together,
wherein the inner sleeve and the outer sleeve form a mechanically mating retention system configured to lock onto the tube.

2. The connector assembly of claim 1, wherein the tubing flange is configured to be permanently and non-removably bonded to the end of the tube.

3. The connector assembly of claim 1, wherein the tubing flange is configured to be integrally formed with the end of the tube.

4. The connector assembly of claim 1, wherein the tubing flange is configured to be bonded to the end of the tube by solvent bonding.

5. The connector assembly of claim 4, wherein the tubing flange is configured to have alike materials with the tube to facilitate solvent bonding.

6. The connector assembly of claim 1, wherein an outer diameter of the head portion is greater than an outer diameter of a proximal portion of the tapering neck portion.

7. The connector assembly of claim 1, wherein the tubing flange comprises a shoulder between the head portion and the tapering neck portion.

8. The connector assembly of claim 1, wherein the proximal portion of the inner sleeve is tapered.

9. The connector assembly of claim 1, wherein the inner sleeve comprises a protrusion positioned along an outer surface of the distal portion of the inner sleeve, and wherein the protrusion is shaped and configured to cooperate with a corresponding groove along an inner surface of the outer sleeve in order to secure the inner sleeve and the outer sleeve in a relative axial position.

10. The connector assembly of claim 1, wherein each of the plurality slots tapers in a distal direction.

11. The connector assembly of claim 1, wherein the inner sleeve comprises an inner surface defining a passage, the passage comprising the receptacle.

12. The connector assembly of claim 1, wherein the receptacle comprises the shoulder at a distal end of the receptacle, the shoulder being configured to reduce distal movement of the head portion of the tubing flange relative to the inner sleeve.

13. The connector assembly of claim 1, wherein the distal portion of the inner sleeve comprises a contoured recessed region, and wherein a proximal-most portion of the contoured recessed region is adjacent to the shoulder.

14. The connector assembly of claim 13, wherein the contoured recessed region opens in a distal direction.

15. The connector assembly of claim 13, wherein the inner sleeve comprises a pair of tabs positioned within the contoured recessed region, the pair of tabs being positioned closer to a proximal end of the contoured recessed region than a distal end of the contoured region, and wherein the inner sleeve comprises a recess positioned between the pair of tabs and the proximal end of the contoured recessed region.

16. The connector assembly of claim 1, wherein the outer sleeve comprises a plurality of prongs, each of the plurality of prongs extending distally and terminating at a free end, the plurality of slots of the inner sleeve configured to receive the plurality of prongs.

17. The connector assembly of claim 16, wherein each of the plurality of prongs comprises a sloped inner surface.

18. The connector assembly of claim 16, further comprising a gap positioned between a distal portion of each of the plurality of prongs and an inner surface of the outer sleeve, the gap being configured to allow a distal portion of each of the plurality of prongs to deflect outwardly away from the axial center of the outer sleeve.

19. The connector assembly of claim 16, wherein the free ends of the plurality of prongs are disposed between the inner sleeve and the tubing flange.

20. The connector assembly of claim 16, wherein the tubing flange further comprises a shoulder on a proximal side of the head portion, the free ends of the plurality of prongs configured to interface with the shoulder on the head portion to limit axial movement of the head portion in a proximal direction.

21. The connector assembly of claim 1, wherein the tubing flange, the inner sleeve, and the outer sleeve are arranged co-axially about a central axis of the tubing flange.

22. The connector assembly of claim 1, wherein a first portion of the gas passageway within the head portion tapers in a first direction, and wherein a second portion of the gas passageway within the tapering neck portion tapers in a second direction opposite the first direction.

23. The connector assembly of claim 22, wherein the first portion tapers in the proximal direction and the second portion tapers in the distal direction.

\* \* \* \* \*